United States Patent
Lundgren et al.

(10) Patent No.: US 8,044,788 B2
(45) Date of Patent: Oct. 25, 2011

(54) WARNING SYSTEM GENERATING WARNING OF DISENGAGEMENT OF PARKING BRAKE OF MOTOR VEHICLE

(75) Inventors: Sten Lundgren, Södertälje (SE); Ola Bergqvist, Nacka (SE)

(73) Assignee: Scania CV AB (SE)

( * ) Notice: Subject to any disclaimer, the term of this patent is extended or adjusted under 35 U.S.C. 154(b) by 746 days.

(21) Appl. No.: 12/089,580

(22) PCT Filed: Sep. 19, 2006

(86) PCT No.: PCT/SE2006/050340
§ 371 (c)(1),
(2), (4) Date: May 2, 2008

(87) PCT Pub. No.: WO2007/043957
PCT Pub. Date: Apr. 19, 2007

(65) Prior Publication Data
US 2008/0224841 A1    Sep. 18, 2008

(30) Foreign Application Priority Data
Oct. 11, 2005    (SE) ..................................... 0502238

(51) Int. Cl.
*B60Q 1/00*    (2006.01)
(52) U.S. Cl. ..................... 340/457.3; 340/453; 340/457; 340/459
(58) Field of Classification Search .................. 340/438, 340/441, 453, 456, 457, 457.3, 459, 460; 307/10.1
See application file for complete search history.

(56) References Cited

U.S. PATENT DOCUMENTS

| | | | |
|---|---|---|---|
| 2,740,947 A | 4/1956 | Davies | |
| 3,381,269 A | 4/1968 | Fierbaugh et al. | |
| 3,651,457 A | 3/1972 | Sprouse | |
| 3,723,968 A * | 3/1973 | Kelly | 340/457.3 |
| 4,482,885 A * | 11/1984 | Mochida | 340/457 |
| 4,495,484 A * | 1/1985 | Kawakatsu et al. | 340/457 |
| 4,877,294 A * | 10/1989 | Kuhn et al. | 303/9 |
| 4,967,182 A | 10/1990 | Foster | |
| 5,394,137 A * | 2/1995 | Orschek | 340/453 |
| 6,015,364 A | 1/2000 | Le Van | |
| 6,246,313 B1 * | 6/2001 | Baker et al. | 340/425.5 |
| 2003/0075981 A1 | 4/2003 | Chen | |

FOREIGN PATENT DOCUMENTS

| | | |
|---|---|---|
| DE | 199 26 697 | 12/2000 |
| JP | 04113069 A * | 4/1992 |

OTHER PUBLICATIONS

International Search Report dated Dec. 20, 2006 issued in corresponding PCT Application No. PCT/SE2006/050340.

* cited by examiner

*Primary Examiner* — Daniel Wu
*Assistant Examiner* — Nay Tun
(74) *Attorney, Agent, or Firm* — Ostrolenk Faber LLP

(57) ABSTRACT

A warning system and a method for alerting a driver of a vehicle that the parking brake of the vehicle is not engaged by generating a warning when the following conditions are simultaneously fulfilled: the ignition of the vehicle is on, the driver access door of the vehicle cabin is open, no throttle lever, or clutch lever or brake lever of the vehicle is activated, the gear shift lever of the vehicle is in the neutral position, and the parking brake is not engaged, and not when—the pressure of a pneumatic circuit associated with the parking brake is below a threshold,—the vehicle speed exceeds a threshold.

19 Claims, 2 Drawing Sheets

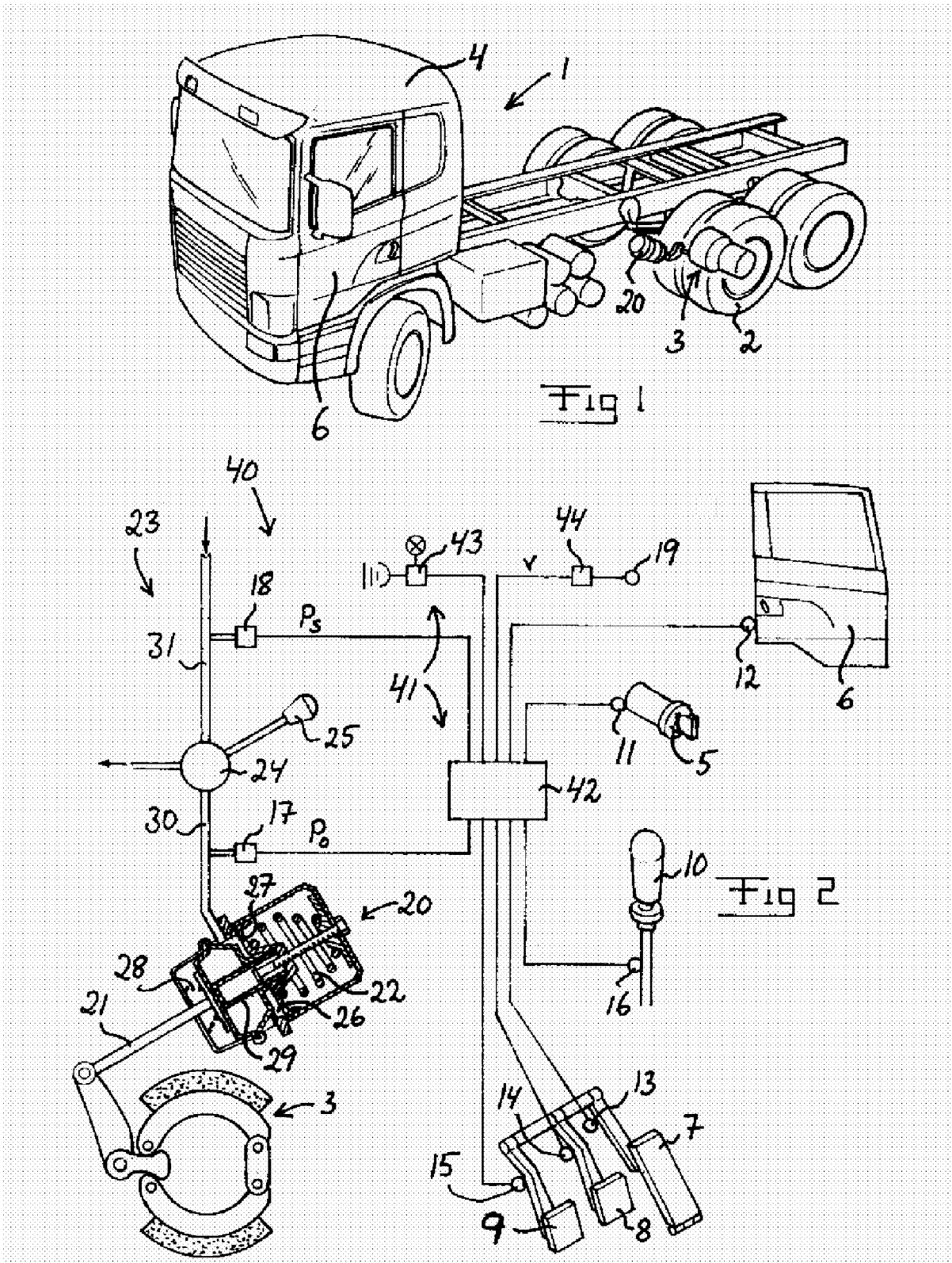

WARNING SYSTEM GENERATING WARNING OF DISENGAGEMENT OF PARKING BRAKE OF MOTOR VEHICLE

CROSS REFERENCE TO RELATED APPLICATION

The present application is a 35 U.S.C. §§371 national phase conversion of PCT/SE2006/050340, filed 19 Sep. 2006, which claims priority of Swedish Application No. 0502238-9, filed 11 Oct. 2005. The PCT International Application was published in the English language.

TECHNICAL FIELD

The present invention relates to a warning system for a motor vehicle provided with a parking brake, wherein the system comprises warning means adapted to generate, under certain predetermined conditions, a warning so as to alert the driver that the parking brake is not engaged. The invention also relates to a method for alerting a driver of a vehicle that the parking brake of the vehicle is not engaged. Furthermore, the invention relates to a computer program comprising computer program code for implementing such a method, a computer program product comprising a data storage medium readable by an electronic control unit and having such a computer program stored thereon, and an electronic control unit.

BACKGROUND ART

If the driver of a vehicle forgets to engage or fails to properly engage the parking brake of the vehicle prior to leaving it when parked on a slope, the vehicle may under its own weight start rolling away. Such accidental situations may cause serious personal injuries and property damage, especially when it comes to heavy motor vehicles such as lorries, towing vehicles or buses. Motor vehicles, such as cars, lorries, towing vehicles and buses, are often provided with a conventional warning function which is activated so as to generate a warning signal when the driver turns off the ignition of the vehicle without having engaged the parking brake, so as to thereby alert the vehicle driver of an inadvertent failure to properly engage the parking brake. On many occasions, however, it is desired to leave the engine running while leaving the vehicle cabin for a short time, e.g. in order to clean the windshield, check a tire, make a delivery etc. On these occasions, said conventional warning function will not be activated due to the fact that the ignition is on when the driver leaves the vehicle cabin, irrespective of whether or not the parking brake is properly engaged. Thus, there is a need of a warning system that may alert the driver that the parking brake is not properly engaged when he/she is about to leave his parked vehicle with the engine still running.

For a parking brake warning system to be efficient, it must generate a rather powerful warning signal so as to insure that the driver before leaving the vehicle really perceives the signal and is alerted of the failure to properly engage the parking brake. However, the warning system should not generate warning signals undesirably, e.g. in situations where the driver, after having stopped the vehicle, intends to remain seated in the vehicle with the parking brake disengaged in order to reverse the vehicle or operate the vehicle in another manner. Such undesired warning signals will annoy the driver and could, if frequently occurring, make the driver less attentive to the warning signal in a situation when he/she actually has omitted to engage the parking brake or even make the driver disable the entire warning system.

A warning system for a motor vehicle provided with a parking brake is previously known from U.S. Pat. No. 3,651,457 A. This known warning system will properly generate a warning signal when the driver opens the driver access door of the vehicle cabin in order to leave the vehicle without having engaged the parking brake. However, this warning system will also generate a warning signal in a situation when the driver intends to remain seated in the vehicle with the driver access door open and the parking brake disengaged, e.g. in order to reverse the vehicle while looking out through the open door. Thus, this known warning system suffers from the above-indicated drawback of undesired warning signals.

A warning system that hypothetically could alleviate the above-indicated problem of undesired warning signals is previously known from U.S. Pat. No. 4,967,182 A. This warning system uses a pressure sensor to sense the pressure on the driver's seat and to close an electric switch whenever the seat is unoccupied. A warning signal is generated if the seat is vacated without the parking brake of the vehicle having been engaged. However, sensors for detecting whether or not the driver's seat is occupied are normally not included as standard components in motor vehicles, which will make it rather costly to implement this known warning system. Furthermore, existing sensors of this type are in general not very reliable, which may result in annoying warning signals during driving or in the lack of warning signals when the driver leaves the vehicle without having engaged the parking brake.

DISCLOSURE OF THE INVENTION

The object of the present invention is to achieve a warning system capable of generating a warning so as to alert the driver of a vehicle that the parking brake is not properly engaged when he/she is about to leave the vehicle cabin while leaving the vehicle engine running and also capable of alleviating the above-indicated problem of undesired warning signals, and which may be implemented in a rather simple and cost-efficient manner.

The object is achieved by means of a warning system having the features described herein.

The inventive warning system comprises warning means adapted to generate a warning so as to alert the driver of the vehicle when the following conditions, optionally in combination with one or several further conditions, are simultaneously fulfilled:
- it is established that the ignition of the vehicle is on,
- it is established that the driver access door of the vehicle cabin is open,
- it is established that no throttle lever, clutch lever or brake lever of the vehicle is activated,
- it is established that the gear shift lever of the vehicle is in the neutral position, and
- it is established that the parking brake is not engaged.

Thus, the warning system according to the present invention will generate a warning when the driver access door of the vehicle cabin is open and the parking brake is disengaged while the engine of the vehicle is running, but only on condition that the driver is not using any throttle lever, clutch lever or brake lever of the vehicle and on condition that the gear shift lever of the vehicle is in the neutral position. The establishment that the driver access door of the vehicle cabin is open at the same time as no throttle lever, clutch lever or brake lever is activated and the gear shift lever of the vehicle is in the neutral position, is in the inventive warning system treated as an indication that the driver intends to leave the vehicle cabin, which implies that the driver is to be alerted if having failed to properly engage the parking brake. By this warning system, the driver of a motor vehicle maybe warned of an inadvertent failure to engage the parking brake of the vehicle immediately upon commencing to leave the vehicle.

The components, such as sensors, control units, warning indicators, etc., required for implementing the inventive system are already included as standard components in many modern motor vehicles. Thus, the warning system according to the invention may be implemented in a simple manner and at low cost.

The establishment that the gear shift lever of the vehicle is in the neutral position could as an alternative condition be changed to that the gear shift lever of the vehicle is not in the reverse gear position, owing to the fact that the manner of sensing engaged gear is different for different types of gearboxes. Which one of these two alternative conditions to use when implementing the invention will consequently depend on the type of gearbox included in the vehicle in question. A vehicle provided with an automatic or a semi-automatic gearbox is provided with means for sensing all the different positions of the gear shift lever. Thus, in this case the condition that the gear shift lever of the vehicle should be in the neutral position is suitably used, since this is the most favourable option suppressing said warning whenever the driver is reversing the vehicle as well as whenever he/she is driving the vehicle slowly forward ("inching") on a low gear. A vehicle provided with a manual gearbox is normally only provided with means for sensing the reverse gear position of the gear shift lever, e.g. in order to control reversing lamps and/or an audible reversing signal. Thus, in this case the condition that the gear shift lever of the vehicle should not be in the reverse gear position is suitably used. A drawback with the last-mentioned option is that the warning might be generated when the driver is driving the vehicle slowly forward ("inching") on a low gear with the driver access door of the cabin open.

The above-indicated warning function of the inventive warning system is intended as a supplement to a conventional warning function which generates a warning signal when the driver turns off the ignition of the vehicle without having engaged the parking brake. Thus, if the inventive warning system is working in parallel with a conventional warning system having said conventional warning function, the conventional warning system is responsible for the generation of a warning when the ignition is off, whereas the inventive warning system should be adapted to refrain from generating any warning when the ignition is off so as to thereby avoid interfering with the conventional warning system. However, if the inventive warning system replaces such a conventional warning system, the function associated with the conventional warning system should be integrated into the inventive warning system, i.e. the inventive warning system should in this case generate a warning whenever the driver turns off the ignition of the vehicle without having engaged the parking brake.

According to an embodiment of the invention, the warning means are adapted to refrain from generating said warning and to cease said warning, if already initiated, if it is established that the supply pressure of the pneumatic circuit associated with the parking brake is below a given threshold value essentially corresponding to the pneumatic operating pressure required for disengaging the parking brake. If said supply pressure is lower than the operating pressure required for disengaging the parking brake, the parking brake will automatically be engaged irrespective of the position of the parking brake lever. Thus, there is no reason to generate said warning if the supply pressure drops to such an extent. Besides, heavy motor vehicles are normally provided with a conventional warning function which is activated so as to generate a warning as soon as said supply pressure drops below the above-indicated threshold value, and it is therefore favourable if the inventive warning system refrains from generating any warning when such a pressure drop occurs so as to thereby avoid interfering with this conventional warning function.

According to another embodiment of the invention, the warning means are adapted to refrain from generating said warning and to cease said warning, if already initiated, if it is established that the vehicle speed exceeds a given threshold value, preferably in the order of 5 km/h. Hereby, a generation of a parking brake warning is prevented during normal driving of the vehicle even if one or more of the sensors that are providing the required input information to the warning system would fail and erroneously indicate that a parking brake warning situation is present.

The invention also relates to a method having the features herein for alerting a driver of a vehicle that the parking brake of the vehicle is not engaged.

The invention also relates to a computer program, a computer program product described herein for storing the computer program, and an electronic control unit described herein of a computer, the electronic control unit executing computer software.

BRIEF DESCRIPTION OF THE DRAWINGS

The invention will in the following be more closely described by means of embodiment examples, with reference to the appended drawings, where:

FIG. 1 is a schematic perspective view of a towing vehicle,

FIG. 2 is a schematic outline diagram illustrating a system according to an embodiment of the present invention.

MODE(S) FOR CARRYING OUT THE INVENTION

Figure 3:
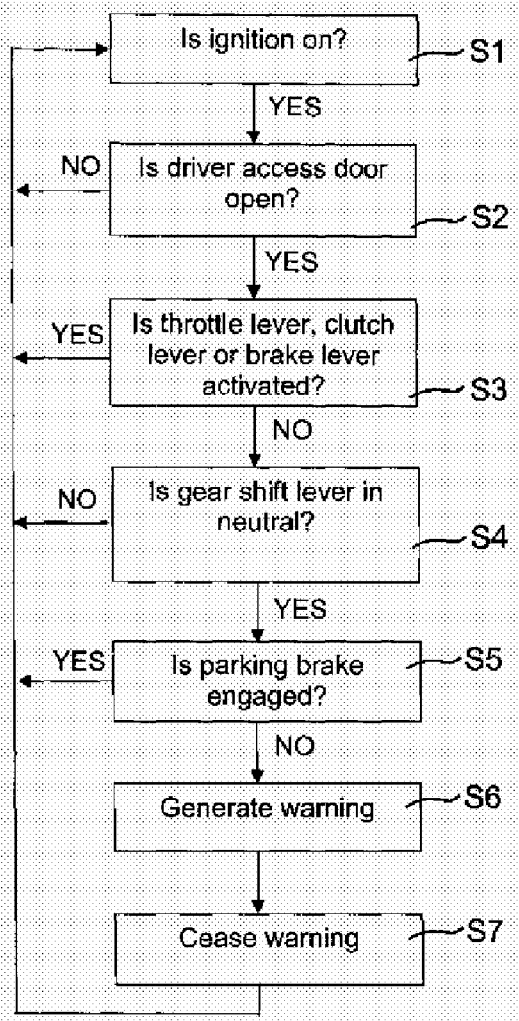
FIG. 3 is a flow diagram illustrating a method according to an embodiment of the invention.

A motor vehicle 1 in the form of a towing vehicle is schematically illustrated in FIG. 1. This vehicle 1 is provided with a pneumatic parking brake circuit including a number of brake cylinders 20, one for each vehicle wheel 2 to be locked by the parking brake. Only the brake cylinder 20 of one of the vehicle wheels 2 is illustrated in FIG. 1. A reciprocable push rod 21 projecting from the brake cylinder 20 is operably connected to braking means 3 for holding the wheel 2 against rotation when the push rod 21 is axially displaced into an advanced position and releasing the wheel for rotation when the push rod 21 is axially displaced into a retracted position. The brake cylinder 20 is of conventional design and is illustrated in longitudinal section in FIG. 2. The push rod 21 is axially displaceable from the advanced position to the retracted position against the action of a compression spring 22. The parking brake is engaged by the action of the compression spring 22 and is released using compressed air from the parking brake circuit 23. In order to disengage the parking brake, the driver actuates a manually operable control valve 24 by means of a parking brake lever 25 located in the vehicle cabin 4 so as to allow compressed air from the parking brake circuit 23 to enter a chamber 26 in the brake cylinder 20.

Hereby, a piston 27 in the brake cylinder will be displaced against the action of the compression spring 22, which allows the push rod 21 to be displaced into the brake cylinder from the advanced position to the retracted position under the action of a return spring 28. In order to engage the parking brake, the driver actuates the control valve 24 by means of a parking brake lever 25 so as to release the compressed air from the chamber 26. Hereby, the piston 27 will be displaced under the action of the compression spring 22 so as to displace the push rod 21, via a second push rod 29 interposed between the piston 27 and the first mentioned push rod 21, from the retracted position to the advanced position against the action of the return spring 28. In order to disengage the parking brake, the operating pressure $P_o$ in the chamber 26, i.e. the pressure of the compressed air introduced into the chamber 26, has to be of a sufficiently high value so as to be able to overcome the spring force of the compression spring 22. If the supply pressure PS of the parking brake circuit 23 drops below this required value, the parking brake will be automatically engaged.

The warning system according to the present invention comprises warning means for generating, under certain predetermined conditions, a warning so as to alert the vehicle driver that the parking brake is not engaged. The generated warning should be perceivable by the driver in the vehicle cabin 4 and is preferably a visible and/or audible warning signal, e.g. in the form of a flashing parking brake symbol on the instrument panel in the vehicle cabin and/or a buzzer.

An embodiment of a warning system 40 according to the present invention is schematically illustrated in FIG. 2. The warning means 41 of this warning system comprise an electronic control unit 42, e.g. constituted by the main electronic control unit of the vehicle, and a warning indicator 43 connected to the electronic control unit. The electronic control unit 42 is arranged to receive:

information as to the turning on and turning off of the ignition 5 of the vehicle,
information as to the opening and closing of the driver access door 6 of the vehicle cabin 4,
information as to the activation of the throttle lever 7, clutch lever 8 and brake lever/levers 9 of the vehicle,
information as to the position of the gear shift lever 10 of the vehicle, and
information as to the engagement and disengagement of the parking brake.

The information as to the turning on and turning off of the ignition 5 of the vehicle may be supplied to the control unit 42 directly from a sensor 11, e.g. in the form of a switch, arranged to sense manoeuvrings of the ignition, or from another control unit connected to such a sensor.

The information as to the opening and closing of the driver access door 6 of the vehicle cabin 4 may be supplied to the control unit 42 directly from a sensor 12, e.g. in the form of a switch, arranged to sense the opening and closing of the door 6, or from another control unit connected to such a sensor.

The information as to the activation of the throttle lever 7 of the vehicle may be supplied to the control unit 42 directly from a sensor 13 arranged to sense manoeuvring movements of the throttle lever 7, or from another control unit connected to such a sensor.

The information as to the activation of the clutch lever 8 of the vehicle may be supplied to the control unit 42 directly from a sensor 14 arranged to sense manoeuvring movements of the clutch lever 7, or from another control unit connected to such a sensor.

The information as to the activation of the brake lever 9 of the vehicle may be supplied to the control unit 42 directly from a sensor 15 arranged to sense manoeuvring movements of the brake lever 9, or from another control unit connected to such a sensor. If the vehicle is provided with two or more brake levers controlling different types of brakes, the respective brake lever should be associated with a sensor and the control unit should be arranged to receive information from each such sensor as to the activation of the respective brake lever.

The information as to the position of the gear shift lever 10 of the vehicle may be supplied to the control unit 42 directly from a sensor 16, e.g. in the form of a switch, arranged to sense the position of the gear shift lever 10, or from another control unit connected to such a sensor.

The information as to the engagement and disengagement of the parking brake may be supplied to the control unit 42 directly from a sensor 17 arranged to sense engagement and disengagement of the parking brake, or from another control unit connected to such a sensor. In the illustrated embodiment, the engagement and disengagement of the parking brake is sensed by means of a pressure sensor 17 arranged to sense the pressure in the air conduit 30 between the control valve 24 and the brake cylinder 20, i.e. the above-indicated operating pressure $P_o$. An operating pressure $P_o$ exceeding a given threshold value corresponding to the pneumatic operating pressure required for disengaging the parking brake indicates that the parking brake is disengaged, and an operating pressure $P_o$ lower than this threshold value indicates that the parking brake is engaged. As an alternative the engagement and disengagement of the parking brake could be sensed by a sensor, such as a switch, arranged to sense the position of the parking brake lever 25.

The electronic control unit 42 is adapted to actuate the warning indicator 43 so as to make the warning indicator generate the above-indicated warning when the following conditions, optionally in combination with one or several further conditions, are simultaneously fulfilled:
it is established that the ignition 5 of the vehicle is on,
it is established that the driver access door 6 of the vehicle cabin is open,
it is established that no throttle lever 7, clutch lever 8 or brake lever 9 of the vehicle is activated,
it is established that the gear shift lever 10 of the vehicle is in the neutral position, and
it is established that the parking brake is not engaged.

After having initiated said warning, the electronic control unit 42 is adapted to cease the warning if any of the following occurs:
it is established that the driver access door 6 of the vehicle cabin has been closed,
it is established that a throttle lever 7, a clutch lever 8 or a brake lever 9 of the vehicle has been activated,
it is established that the gear shift lever 10 of the vehicle has been moved away, i.e. shifted, from the neutral position or that the gear shift lever of the vehicle has been moved, or
it is established that the parking brake has been engaged.

Furthermore, the electronic control unit 42 should be adapted to cease the warning when a predetermined period of time has elapsed since the initiation of the warning if the warning has not been stopped before that.

The warning means 41 are suitably adapted to refrain from generating said warning and to cease said warning, if already initiated, if it is established that the supply pressure $P_s$ of the pneumatic circuit 23 associated with the parking brake is below a given threshold value $P_t$ essentially corresponding to the pneumatic operating pressure $P_o$ required for disengaging the parking brake. In this case, the control unit 42 is arranged to receive information as to said supply pressure $P_s$, either directly from a pressure sensor 18 arranged to sense the pressure in an air conduit 31 of the parking brake circuit 23 upstream of the control valve 24 or from another control unit connected to such a pressure sensor.

Furthermore, the warning means 41 are suitably adapted to refrain from generating said warning and to cease said warning, if already initiated, if it is established that the vehicle speed v exceeds a given threshold value $v_t$, preferably in the order of 5 km/h. In this case, the control unit 42 is arranged to receive information as to the vehicle speed, either directly from a speed sensor 19 arranged to sense the vehicle speed or from another control unit 44 connected to such a speed sensor.

Preferably, the warning means 41 are adapted to generate a warning also if it is established that the parking brake is not engaged when it is established that the ignition 5 of the vehicle is turned off. This warning should be stopped if it is established that the parking brake is engaged or that the ignition is turned on or when a predetermined period of time has elapsed since the initiation of the warning if the warning has not been stopped before that.

A flow diagram illustrating a method according to an embodiment of the invention is shown in FIG. 3. In a first step S1, it is established whether or not the ignition of the vehicle is on. In a second step S2, it is established whether or not the driver access door of the vehicle cabin is open. In a third step S3, it is established whether or not a throttle lever, a clutch lever or a brake lever of the vehicle is activated. In a fourth step S4, it is established whether or not the gear shift lever of the vehicle is in the neutral position. In a fifth step S5, it is established whether or not the parking brake of the vehicle is engaged. If it is established in these steps S1-S5:
  that the ignition of the vehicle is on,
  that the driver access door of the vehicle cabin is open,
  that no throttle lever, clutch lever or brake lever of the vehicle is activated,
  that the gear shift lever of the vehicle is in the neutral position, and
  that the parking brake is not engaged,
then a warning perceivable in the vehicle cabin is generated in a sixth step S6. The warning will then be stopped in a seventh step S7 under the previously indicated conditions. The above-indicated steps S1-S5 may be executed essentially simultaneously and in any desired order.

Computer program code for implementing a method according to the invention is suitably included in a computer program, which is loadable directly into the internal memory of a computer, such as the internal memory of the main electronic control unit of the vehicle. Such a computer program is suitably provided via a computer program product comprising a data storage medium readable by an electronic control unit, which data storage medium has the computer program stored thereon. Said data storage medium is for instance an optical data storage medium in the form of a CD-ROM disc, a DVD disc etc, or a magnetic data storage medium in the form of a hard disc, a diskette, a cassette tape etc.

The computer program according to an embodiment of the invention comprises computer program code for causing a computer, e.g. in the form of an electronic control unit comprising a microprocessor or the like data processing unit:
  to establish whether or not the ignition of a vehicle is on,
  to establish whether or not the driver access door of the vehicle cabin is open,
  to establish whether or not a throttle lever, a clutch lever or a brake lever of the vehicle is activated,
  to establish whether or not the gear shift lever of the vehicle is in the neutral position,
  to establish whether or not the parking brake is engaged, and
  to initiate a generation of a warning, preferably in the form of a visible and/or audible warning signal, so as to alert the driver of the vehicle when the following conditions, optionally in combination with one or several further conditions, are simultaneously fulfilled:
    the ignition of the vehicle is on,
    the driver access door of the vehicle cabin is open,
    no throttle lever, clutch lever or brake lever of the vehicle is activated,
    the gear shift lever of the vehicle is in the neutral position, and
    the parking brake is not engaged.

Figure 4:
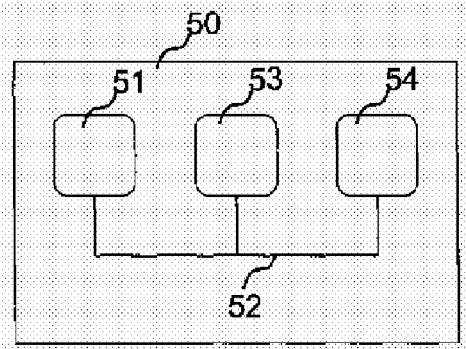
FIG. 4 is a schematic outline diagram of an electronic control unit for implementing a method according to the invention.

FIG. 4 very schematically illustrates an electronic control unit 50 comprising an execution means 51, such as a central processing unit (CPU), for executing computer software. The execution means 51 communicates with a memory 53, for instance of the type RAM, via a data bus 52. The control unit 50 also comprises data storage medium 54, for instance in the form of a memory of the type ROM, PROM, EPROM or EEPROM or a Flash memory. The execution means 51 communicates with the data storage medium 54 via the data bus 52. A computer program comprising computer program code for implementing a method according to the invention is stored on the data storage medium 54.

The inventive warning system is intended to be used in a motor vehicle, such as for instance a car, a lorry, a towing vehicle or a bus.

The invention is of course not in any way restricted to the embodiments described above. On the contrary, many possibilities to modifications thereof will be apparent to a person with ordinary skill in the art without departing from the basic idea of the invention as defined in the appended claims.

The invention claimed is:

1. A warning system for a motor vehicle provided with a parking brake, wherein the system comprises a warning device operable to determine occurrence of each of the following conditions and to generate a warning signal, when the following conditions, are simultaneously fulfilled:
  an ignition of the vehicle is on,
  a driver access door of the vehicle cabin is open,
  no throttle lever, clutch lever or brake lever of the vehicle is activated,
  a gear shift lever of the vehicle is in a neutral position, and
  a parking brake is not engaged.

2. A warning system according to claim 1, wherein the warning device is operable to not generate a warning if any of the following occurs:
  the driver access door of the vehicle cabin is closed,
  a throttle lever, a clutch lever or a brake lever of the vehicle has been activated,
  the gear shift lever of the vehicle is not in the neutral position, or
  the parking brake has been engaged.

3. A warning system according to claim 2, wherein the warning device comprises an electronic control unit and a warning indicator connected to the electronic control unit;
  the electronic control unit being operable to receive:
    information as to the turning on and turning off the ignition of the vehicle,
    information as to the opening and closing of the driver access door of the vehicle cabin,
    information as to the activation of a throttle lever, clutch lever or brake lever of the vehicle, information as to a position of the gear shift lever of the vehicle, and information as to the engagement and disengagement of the parking brake; and the electronic control unit being operable to actuate the warning indicator to generate that warning when all of the aforementioned conditions are simultaneously fulfilled.

4. A warning system according to claim 3, further comprising a pneumatic circuit associated with the parking brake; and wherein the warning device is operable not to generate the warning when a supply pressure ($P_s$) of the pneumatic circuit associated with the parking brake is below a given threshold value ($P_t$) essentially corresponding to a pneumatic operating pressure ($P_o$) required for disengaging the parking brake.

5. A warning system according claim 3, wherein the warning device refrains from generating the warning when the vehicle speed (v) exceeds a threshold value ($v_t$).

6. A warning system according to claim 3, wherein, the warning device is operable to generate a warning when the parking brake is not engaged and an ignition of the vehicle is turned off.

7. A warning system according to claim 1, wherein the warning is at least one of a visible and an audible warning signal.

8. A method for alerting a driver of a vehicle that a parking brake of the vehicle is not engaged comprising generating a warning when the following conditions are simultaneously fulfilled:

an ignition of the vehicle is on,
a driver access door of a vehicle cabin is open,
no throttle lever, clutch lever or brake lever of the vehicle is activated,
a gear shift lever of the vehicle is in the neutral position, and
the parking brake is not engaged.

9. A method according to claim 8 further comprising not generating a warning if any of the following occurs:

the driver access door of the vehicle cabin has been closed,
a throttle lever, a clutch lever or a brake lever of the vehicle has been activated,
the gear shift lever of the vehicle has been shifted from the neutral position, or
the parking brake has been engaged.

10. A method according to claim 9, wherein the warning is not generated when determining that a supply pressure ($P_s$) of a pneumatic circuit associated with the parking brake is below a given threshold value ($P_t$) essentially corresponding to a pneumatic operating pressure ($P_o$) required for disengaging the parking brake.

11. A method according to claim 9 wherein the warning is not generated when a vehicle speed (v) exceeds a given threshold value ($v_t$).

12. A method according to claim 9, wherein a warning is generated if the parking brake is not engaged when the ignition of the vehicle is turned off.

13. A computer program loadable directly into an internal memory of a computer, the computer program being stored on a non-transitory computer-readable medium, wherein that computer program comprises computer program code for causing the computer:

to establish whether or not an ignition of a vehicle is on,
to establish whether or not a driver access door of the vehicle cabin is open,
to establish whether or not a throttle lever, a clutch lever or a brake lever of the vehicle is activated,
to establish whether or not a gear shift lever of the vehicle is in a neutral position,
to establish whether or not a parking brake of the vehicle is engaged, and
to initiate a generation of a warning, to alert a driver of the vehicle when the following conditions are simultaneously fulfilled:
the ignition of the vehicle is on,
the driver access door of the vehicle cabin is open,
no throttle lever, clutch lever or brake lever of the vehicle is activated,
the gear shift lever of the vehicle is in the neutral position, and
the parking brake is not engaged.

14. A computer program according to claim 13, wherein the computer program comprises computer program code for causing the computer to cease the warning if any of the following occurs:

the driver access door of the vehicle cabin has been closed,
a throttle lever, a clutch lever or a brake lever of the vehicle has been activated,
the gear shift lever of the vehicle has been shifted from the neutral position, or
the parking brake has been engaged.

15. A computer program according to claim 14, wherein the computer program comprises computer program code for causing the computer:

to establish whether or not a supply pressure ($P_s$) of a pneumatic circuit associated with the parking brake is below a given threshold value ($P_t$) essentially corresponding to the pneumatic operating pressure ($P_o$) required for disengaging the parking brake, and
to refrain from generation of said warning if the supply pressure ($P_s$) is below the given threshold value ($P_t$).

16. A computer program according to claim 13, wherein the computer program comprises computer program code for causing the computer:

to establish whether or not the vehicle speed (v) exceeds a given threshold value ($v_t$), and
to refrain from initiating a generation of said warning if it is established that the vehicle speed (v) exceeds the given threshold value ($v_t$).

17. A computer program according to claim 13, wherein the computer program comprises computer program code for causing the computer to generate a warning if the parking brake is not engaged when the ignition of the vehicle is turned off.

18. A computer program product comprising a non-transitory data storage medium readable by an electronic control unit, and a computer program according to claim 17 being stored on said non-transitory data storage medium.

19. An electronic control unit comprising an execution means, a memory connected to the execution means and a data storage medium connected to the execution means, and a computer program according to claim 18 stored on the non-transitory data storage medium.

* * * * *